US009051361B2

(12) United States Patent
Chong et al.

(10) Patent No.: US 9,051,361 B2
(45) Date of Patent: Jun. 9, 2015

(54) IMMUNOGENIC COMPOSITIONS AND USES THEREOF

(75) Inventors: Pele Choi-Sing Chong, Miaoli County (TW); Chia-Chyi Liu, Taichung County (TW); Meng-Shin Kuo, Miaoli County (TW); Ray Jui-Yuan Chang, Yilan County (TW)

(73) Assignee: National Health Research Institutes, Zhunan Town (TW)

( * ) Notice: Subject to any disclaimer, the term of this patent is extended or adjusted under 35 U.S.C. 154(b) by 882 days.

(21) Appl. No.: 12/858,007

(22) Filed: Aug. 17, 2010

(65) Prior Publication Data

US 2012/0045468 A1 Feb. 23, 2012

(51) Int. Cl.

| | |
|---|---|
| *A61K 39/125* | (2006.01) |
| *C12N 7/00* | (2006.01) |
| *A61K 45/06* | (2006.01) |
| *A61K 39/39* | (2006.01) |
| *C07K 16/10* | (2006.01) |
| *C07K 14/005* | (2006.01) |
| *A61K 39/00* | (2006.01) |

(52) U.S. Cl.
CPC ........... *C07K 16/1009* (2013.01); *A61K 39/125* (2013.01); *C07K 2317/34* (2013.01); *C12N 2770/32334* (2013.01); *A61K 2039/5252* (2013.01); *C07K 14/005* (2013.01); *C12N 7/00* (2013.01); *C12N 2770/32322* (2013.01); *C12N 2770/32351* (2013.01); *C12N 2770/32363* (2013.01); *A61K 2039/55505* (2013.01)

(58) Field of Classification Search
None
See application file for complete search history.

(56) References Cited

U.S. PATENT DOCUMENTS

| | | | | |
|---|---|---|---|---|
| 5,719,051 | A | 2/1998 | Mundt et al. | |
| 6,455,298 | B1 | 9/2002 | Groner et al. | |
| 8,168,192 | B2 * | 5/2012 | Chen et al. | 424/186.1 |
| 2006/0153870 | A1 * | 7/2006 | Parks et al. | 424/204.1 |

OTHER PUBLICATIONS

Wu et al. (Vaccine, 2002, vol. 20, p. 895-904).*
Liu et al. (Vaccine, 2007, vol. 25, p. 19-24 in IDS on Mar. 1, 2012).*
Luo et al. (Emerging Infectious Diseases, Apr. 2009, vol. 15, p. 581-584).*
Wu, Suh-Chin, et al. "Optimization of microcarrier cell culture process for the inactivated enterovirus type 71vaccine development" *Vaccine*, 22 (2004) pp. 3858-3864.

Liu, Chia-Chyi, et al. "High immunogenic enterovirus 71 strain and its production using serum-free microcarrier Vero cell structure" *Vaccine* 25 (2007) pp. 19-24.

Damian Guang Wei Foo, et al. "Passive protection against lethal enterovirus 71 infection in newborn mice by neutralizing antibodies elected by a synthetic peptide" *Microbes and Infection* 9 (2007) pp. 1299-1306.

Damian Guang Wei Foo, et al. "Identification of neutralizing linear epitopes from the VP1 capsid protein of Enterovirus 71 using synthetic peptides" *Virus Research* 125 (2007) pp. 61-68.

* cited by examiner

*Primary Examiner* — Agnieszka Boesen

(74) *Attorney, Agent, or Firm* — Cesari and McKenna, LLP

(57) ABSTRACT

Disclosed are methods of producing a purified EV71 virus antigen. Also disclosed are related immunogenic compositions and immunization methods.

6 Claims, 10 Drawing Sheets

SEQUENCE LISTING

<160> NUMBER OF SEQ ID NOS: 49

<210> SEQ ID NO 1
<211> LENGTH: 25
<212> TYPE: PRT

```
<213> ORGANISM: Artificial Sequence
<220> FEATURE:
<223> OTHER INFORMATION: Synthetic peptide

<400> SEQUENCE: 1

Val Ile Gly Thr Val Ala Gly Gly Thr Gly Thr Glu Asn Ser His Pro
1               5                   10                  15

Pro Tyr Lys Gln Thr Gln Pro Gly Ala
            20                  25

<210> SEQ ID NO 2
<211> LENGTH: 25
<212> TYPE: PRT
<213> ORGANISM: Artificial Sequence
<220> FEATURE:
<223> OTHER INFORMATION: Synthetic peptide

<400> SEQUENCE: 2

Val Ile Gly Thr Val Ala Gly Gly Thr Gly Thr Glu Asp Ser His Pro
1               5                   10                  15

Pro Tyr Lys Gln Thr Gln Pro Gly Ala
            20                  25

<210> SEQ ID NO 3
<211> LENGTH: 25
<212> TYPE: PRT
<213> ORGANISM: Artificial Sequence
<220> FEATURE:
<223> OTHER INFORMATION: Synthetic peptide

<400> SEQUENCE: 3

Val Ile Gly Thr Val Ala Gly Gly Thr Gly Thr Glu Asn Ser His His
1               5                   10                  15

Pro Tyr Lys Gln Thr Gln Pro Gly Ala
            20                  25

<210> SEQ ID NO 4
<211> LENGTH: 25
<212> TYPE: PRT
<213> ORGANISM: Artificial Sequence
<220> FEATURE:
<223> OTHER INFORMATION: Synthetic peptide

<400> SEQUENCE: 4

Val Ile Gly Thr Val Ala Gly Gly Thr Gly Thr Glu Asp Ser His His
1               5                   10                  15

Pro Tyr Lys Gln Thr Gln Pro Gly Ala
            20                  25

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide

<400> SEQUENCE: 5

Gly Asp Arg Val Ala Asp Val Ile Glu Ser Ser Ile Gly Asp Ser
1               5                   10                  15

<210> SEQ ID NO 6
<211> LENGTH: 15
<212> TYPE: PRT
<213> ORGANISM: Artificial Sequence
<220> FEATURE:
```

```
<223> OTHER INFORMATION: Synthetic peptide

<400> SEQUENCE: 6

Asp Gly Tyr Pro Thr Phe Gly Glu His Lys Gln Glu Lys Asp Leu
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

Phe Gly Glu His Lys Gln Glu Lys Asp Leu Glu Tyr Gly Ala Cys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

Val Ile Gly Thr Val Ala Gly Gly Thr Gly Thr Glu Asp Ser His
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide

<400> SEQUENCE: 9

Ala Gly Gly Thr Gly Thr Glu Asp Ser His Pro Pro Tyr Lys Gln
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Thr Glu Asp Ser His Pro Pro Tyr Lys Gln Thr Gln Pro Gly Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Ala Gly Glu His Lys Gln Glu Lys Asp Leu Glu Tyr Gly Ala Cys
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 12

Phe Ala Glu His Lys Gln Glu Lys Asp Leu Glu Tyr Gly Ala Cys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Phe Gly Ala His Lys Gln Glu Lys Asp Leu Glu Tyr Gly Ala Cys
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic peptide

<400> SEQUENCE: 14

Phe Gly Glu Ala Lys Gln Glu Lys Asp Leu Glu Tyr Gly Ala Cys
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide

<400> SEQUENCE: 15

Phe Gly Glu His Ala Gln Glu Lys Asp Leu Glu Tyr Gly Ala Cys
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide

<400> SEQUENCE: 16

Phe Gly Glu His Lys Ala Glu Lys Asp Leu Glu Tyr Gly Ala Cys
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic peptide

<400> SEQUENCE: 17

Phe Gly Glu His Lys Gln Ala Lys Asp Leu Glu Tyr Gly Ala Cys
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide
```

```
<400> SEQUENCE: 18

Phe Gly Glu His Lys Gln Glu Ala Asp Leu Glu Tyr Gly Ala Cys
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic peptide

<400> SEQUENCE: 19

Phe Gly Glu His Lys Gln Glu Lys Ala Leu Glu Tyr Gly Ala Cys
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic peptide

<400> SEQUENCE: 20

Phe Gly Glu His Lys Gln Glu Lys Asp Ala Glu Tyr Gly Ala Cys
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic peptide

<400> SEQUENCE: 21

Phe Gly Glu His Lys Gln Glu Lys Asp Leu Ala Tyr Gly Ala Cys
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Synthetic peptide

<400> SEQUENCE: 22

Phe Gly Glu His Lys Gln Glu Lys Asp Leu Glu Ala Gly Ala Cys
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic peptide

<400> SEQUENCE: 23

Phe Gly Glu His Lys Gln Glu Lys Asp Leu Glu Tyr Ala Ala Cys
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide

<400> SEQUENCE: 24
```

```
Phe Gly Glu His Lys Gln Glu Lys Asp Leu Glu Tyr Gly Ala Ala
1               5                   10                  15
```

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide

<400> SEQUENCE: 25

```
Ala Ala Gly Thr Gly Thr Glu Asp Ser His Pro Pro Tyr Lys Gln
1               5                   10                  15
```

<210> SEQ ID NO 26
<211> LENGTH: 15
<212> TYPE: PRT
<213> ORGANISM: Artificial Sequence
<220> FEATURE:
<223> OTHER INFORMATION: Synthetic peptide

<400> SEQUENCE: 26

```
Ala Gly Ala Thr Gly Thr Glu Asp Ser His Pro Pro Tyr Lys Gln
1               5                   10                  15
```

<210> SEQ ID NO 27
<211> LENGTH: 15
<212> TYPE: PRT
<213> ORGANISM: Artificial Sequence
<220> FEATURE:
<223> OTHER INFORMATION: Synthetic peptide

<400> SEQUENCE: 27

```
Ala Gly Gly Ala Gly Thr Glu Asp Ser His Pro Pro Tyr Lys Gln
1               5                   10                  15
```

<210> SEQ ID NO 28
<211> LENGTH: 15
<212> TYPE: PRT
<213> ORGANISM: Artificial Sequence
<220> FEATURE:
<223> OTHER INFORMATION: Synthetic peptide

<400> SEQUENCE: 28

```
Ala Gly Gly Thr Ala Thr Glu Asp Ser His Pro Pro Tyr Lys Gln
1               5                   10                  15
```

<210> SEQ ID NO 29
<211> LENGTH: 15
<212> TYPE: PRT
<213> ORGANISM: Artificial Sequence
<220> FEATURE:
<223> OTHER INFORMATION: Synthetic peptide

<400> SEQUENCE: 29

```
Ala Gly Gly Thr Gly Ala Glu Asp Ser His Pro Pro Tyr Lys Gln
1               5                   10                  15
```

<210> SEQ ID NO 30
<211> LENGTH: 15
<212> TYPE: PRT
<213> ORGANISM: Artificial Sequence
<220> FEATURE:
<223> OTHER INFORMATION: Synthetic peptide

<400> SEQUENCE: 30

Ala Gly Gly Thr Gly Thr Ala Asp Ser His Pro Pro Tyr Lys Gln
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Synthetic peptide

<400> SEQUENCE: 31

Ala Gly Gly Thr Gly Thr Glu Ala Ser His Pro Pro Tyr Lys Gln
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic peptide

<400> SEQUENCE: 32

Ala Gly Gly Thr Gly Thr Glu Asp Ala His Pro Pro Tyr Lys Gln
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Synthetic peptide

<400> SEQUENCE: 33

Ala Gly Gly Thr Gly Thr Glu Asp Ser Ala Pro Pro Tyr Lys Gln
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Synthetic peptide

<400> SEQUENCE: 34

Ala Gly Gly Thr Gly Thr Glu Asp Ser His Ala Pro Tyr Lys Gln
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetic peptide

<400> SEQUENCE: 35

Ala Gly Gly Thr Gly Thr Glu Asp Ser His Pro Ala Tyr Lys Gln
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetic peptide

<400> SEQUENCE: 36

Ala Gly Gly Thr Gly Thr Glu Asp Ser His Pro Pro Ala Lys Gln

```
1               5                  10                  15
```

<210> SEQ ID NO 37
<211> LENGTH: 15
<212> TYPE: PRT
<213> ORGANISM: Artificial Sequence
<220> FEATURE:
<223> OTHER INFORMATION: Synthetic peptide

<400> SEQUENCE: 37

```
Ala Gly Gly Thr Gly Thr Glu Asp Ser His Pro Pro Tyr Ala Gln
1               5                  10                  15
```

<210> SEQ ID NO 38
<211> LENGTH: 15
<212> TYPE: PRT
<213> ORGANISM: Artificial Sequence
<220> FEATURE:
<223> OTHER INFORMATION: Synthetic peptide

<400> SEQUENCE: 38

```
Ala Gly Gly Thr Gly Thr Glu Asp Ser His Pro Pro Tyr Lys Ala
1               5                  10                  15
```

<210> SEQ ID NO 39
<211> LENGTH: 15
<212> TYPE: PRT
<213> ORGANISM: Artificial Sequence
<220> FEATURE:
<223> OTHER INFORMATION: Synthetic peptide

<400> SEQUENCE: 39

```
Arg Lys Val Glu Leu Phe Thr Tyr Met Arg Phe Asp Ala Glu Phe
1               5                  10                  15
```

<210> SEQ ID NO 40
<211> LENGTH: 15
<212> TYPE: PRT
<213> ORGANISM: Artificial Sequence
<220> FEATURE:
<223> OTHER INFORMATION: Synthetic peptide

<400> SEQUENCE: 40

```
Ser Lys Ser Lys Tyr Pro Leu Val Ile Arg Ile Tyr Met Arg Met
1               5                  10                  15
```

<210> SEQ ID NO 41
<211> LENGTH: 15
<212> TYPE: PRT
<213> ORGANISM: Artificial Sequence
<220> FEATURE:
<223> OTHER INFORMATION: Synthetic peptide

<400> SEQUENCE: 41

```
Pro Leu Val Ile Arg Ile Tyr Met Arg Met Lys His Val Arg Ala
1               5                  10                  15
```

<210> SEQ ID NO 42
<211> LENGTH: 15
<212> TYPE: PRT
<213> ORGANISM: Artificial Sequence
<220> FEATURE:
<223> OTHER INFORMATION: Synthetic peptide

<400> SEQUENCE: 42

```
Ala Gln Phe His Tyr Leu Tyr Arg Ser Gly Phe Cys Ile His Val
1               5                  10                  15
```

<210> SEQ ID NO 43
<211> LENGTH: 15
<212> TYPE: PRT
<213> ORGANISM: Artificial Sequence
<220> FEATURE:
<223> OTHER INFORMATION: Synthetic peptide

<400> SEQUENCE: 43

```
Gly Tyr Tyr Thr Gln Trp Ser Gly Ser Leu Glu Val Thr Phe Met
1               5                   10                  15
```

<210> SEQ ID NO 44
<211> LENGTH: 15
<212> TYPE: PRT
<213> ORGANISM: Artificial Sequence
<220> FEATURE:
<223> OTHER INFORMATION: Synthetic peptide

<400> SEQUENCE: 44

```
Arg Lys Val Glu Leu Phe Thr Asp Met Arg Phe Asp Ala Glu Phe
1               5                   10                  15
```

<210> SEQ ID NO 45
<211> LENGTH: 15
<212> TYPE: PRT
<213> ORGANISM: Artificial Sequence
<220> FEATURE:
<223> OTHER INFORMATION: Synthetic peptide

<400> SEQUENCE: 45

```
Ser Lys Ser Lys Tyr Pro Leu Val Val Arg Ile Tyr Met Arg Met
1               5                   10                  15
```

<210> SEQ ID NO 46
<211> LENGTH: 15
<212> TYPE: PRT
<213> ORGANISM: Artificial Sequence
<220> FEATURE:
<223> OTHER INFORMATION: Synthetic peptide

<400> SEQUENCE: 46

```
Ser Lys Ser Glu Tyr Ser Leu Val Ile Arg Ile Tyr Met Arg Met
1               5                   10                  15
```

<210> SEQ ID NO 47
<211> LENGTH: 20
<212> TYPE: PRT
<213> ORGANISM: Artificial Sequence
<220> FEATURE:
<223> OTHER INFORMATION: Synthetic peptide

<400> SEQUENCE: 47

```
Ser Lys Ser Glu Tyr Ser Leu Val Ile Arg Ile Tyr Met Arg Met Lys
1               5                   10                  15

His Val Arg Ala
            20
```

<210> SEQ ID NO 48
<211> LENGTH: 20
<212> TYPE: PRT
<213> ORGANISM: Artificial Sequence
<220> FEATURE:
<223> OTHER INFORMATION: Synthetic peptide

<400> SEQUENCE: 48

```
Ser Lys Ser Lys Tyr Pro Leu Val Ile Arg Ile Tyr Met Arg Met Lys
1               5                   10                  15

His Val Arg Ala
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic peptide

<400> SEQUENCE: 49

Ser Lys Ser Lys Tyr Pro Leu Val Val Arg Ile Tyr Met Arg Met Lys
1               5                   10                  15

His Val Arg Ala
            20
```

IMMUNOGENIC COMPOSITIONS AND USES THEREOF

BACKGROUND

Viral infection causes various disorders. For example, Enterovirus 71 (EV-71) is one of the major causative agents for hand, foot and mouth disease, and is associated with severe neurological diseases. As little is known about the molecular mechanisms of host response to EV71 infection, no effective antiviral agent is available to combat EV71 infection. There is a need for an effective vaccine against EV71 infection.

SUMMARY

This invention relates to immunogenic compositions (e.g., vaccines) against EV71 infection and related methods.

Accordingly, one aspect of this invention features a method of producing a purified EV71 virus antigen, which can be used to make immunogenic compositions (e.g., vaccines) against EV71 infection. The method includes culturing a cell producing an EV71 virus in a culture medium, purifying an EV71 virus (either a full particle or a sub-particle) from the cell or the medium, and inactivating the purified EV71 virus to obtain the purified EV71 virus antigen. Preferably, the culture medium is a serum-free medium. The purifying step can be conducted by liquid chromatography purification, sucrose gradient ultracentrifuge purification, or both. The inactivating step can be conducted by incubating the EV71 virus in a solution containing formaldehyde at 20-45° C. for 2 to 20 days, e.g., at 20-40° C. for 2 to 10 days, or at about 37° C. for 2 to 5 days. The culturing step can be conducted in a roller bottle or a microcarrier bioreactor. In one embodiment, the method further includes a step of determining the amount of the purified EV71 virus antigen. This determining step can be conducted by quantitative ELISA. In the above method, the EV71 virus antigen can be an isolated EV71 virus full-particle, an isolated EV71 virus sub-particle, or an isolated EV71 virus protein. These antigens can be used in an immunogenic composition. Thus, in another aspect, the invention features an immunogenic composition containing a purified EV71 virus antigen.

An isolated virus particle, protein, polypeptide or peptide refers to a virus particle, protein, polypeptide, or peptide substantially free from naturally associated molecules, i.e., it is at least 75% (i.e., any number between 75% and 100%, inclusive) pure by dry weight. Purity can be measured by any appropriate standard method, e.g., by column chromatography, polyacrylamide gel electrophoresis, or HPLC analysis. An isolated peptide, polypeptide or protein can be purified from a natural source, produced by recombinant DNA techniques, or by chemical methods. The terms protein and polypeptide are used interchangably to describe any chain of amino acids, regardless of length or post-translational modification (for example, glycosylation or phosphorylation). Thus, the term "polypeptides of the invention" includes: full-length, naturally occurring proteins of the invention; recombinantly or synthetically produced polypeptides that correspond to full-length naturally occurring proteins of the invention; or particular domains or portions of the naturally occurring proteins. The term also encompasses mature polypeptides that have an added amino-terminal methionine (useful for expression in prokaryotic cells). A peptide refers to chains that are short enough to be made synthetically from the constituent amino acids. Generally, a peptide is 50 amino acid residues in length or shorter (e.g., 50, 40, 30, 20, 15, 10, or 5 residues in length). A virus full-particle or a complete virus particle refers to a virion that consists of nucleic acid (its genome) surrounded by a protective coat of protein, i.e., a capsid. A sub-particle refers to a particle that contains the capsid, but an incomplete genome or no nucleic acid. See, e.g., Kinpe D M. and Howley P M. (2001) Fundamental Virology, 4$^{th}$ Edition, Chapter 18.

Examples of the EV71 virus protein include a first EV71 virus polypeptide that includes a fragment or peptide of EV71 VP1 protein that has or consists of a sequence selected from the group consisting of SEQ ID NOs: 5-7, 11-14, 16, 20-24, 39-41, and 44-46 (listed below); and a second EV71 virus polypeptide that includes a fragment or peptide of EV71 VP2 or VP3 protein. The immunogenic composition can further include a pharmaceu-tically acceptable adjuvant, such as aluminum phosphate. The first or second EV71 virus polypeptide is at least 15 amino acid residues in length. The second EV71 virus polypeptide can include or consists of a sequence selected from the group consisting of SEQ ID NOs: 1-4, 8-10, 25-29, 31-32, 34-35, 38, 42, and 43 (listed below).

The above-described antigens or compositions can be used in inducing an immune response to enterovirus infection. To that end, one can administer to a subject in need thereof an effective amount of the antigens or compositions. A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds. In a preferred embodiment, the subject is a human, especially young children. In another embodiment, the subject is an experimental animal or animal suitable as a disease model.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
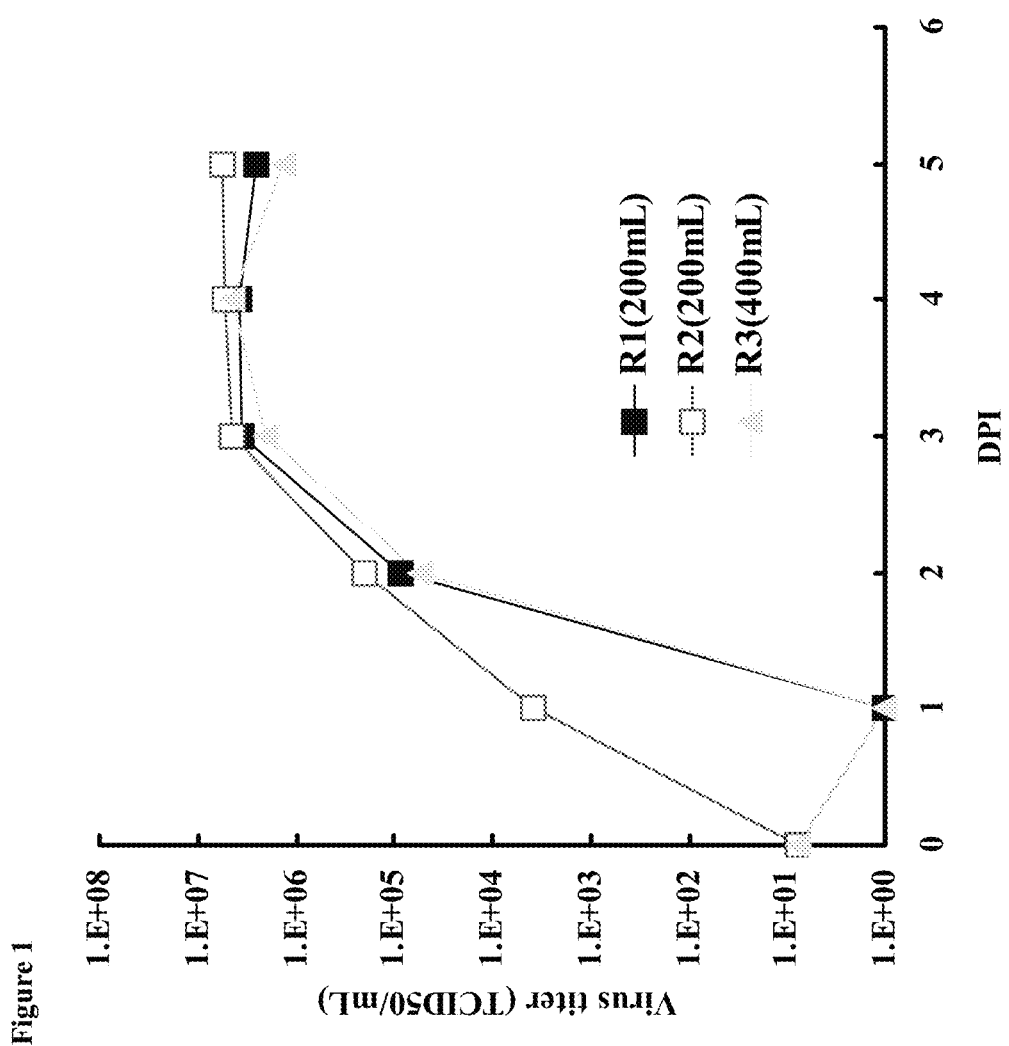
FIG. 1 is a diagram showing production of EV71-E59 viral stocks in a roller bottle.
Figure 2:
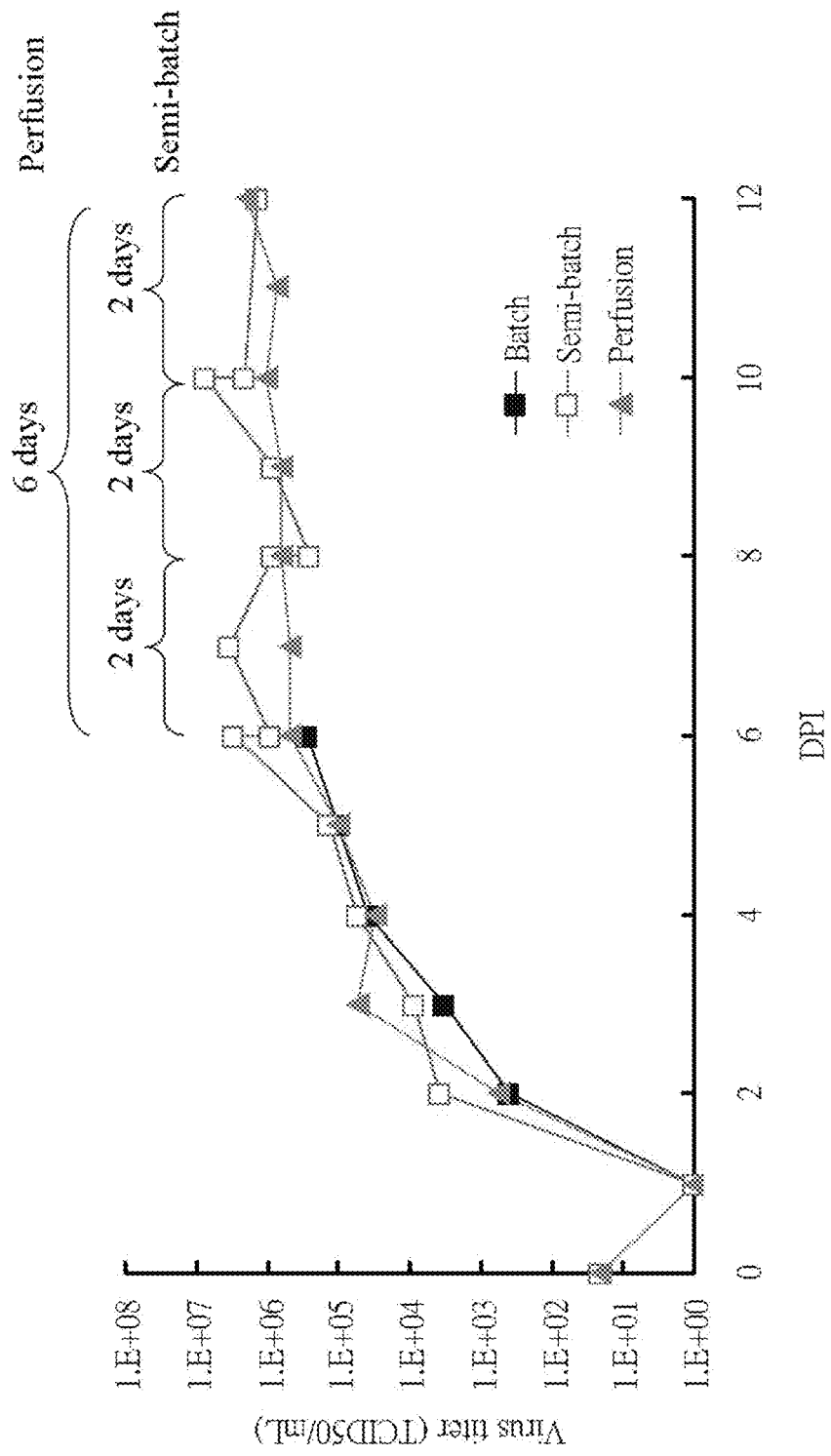
FIG. 2 is a diagram showing production of EV71-E59 viral stocks in a 1.4 L bioreactor.
Figure 3:
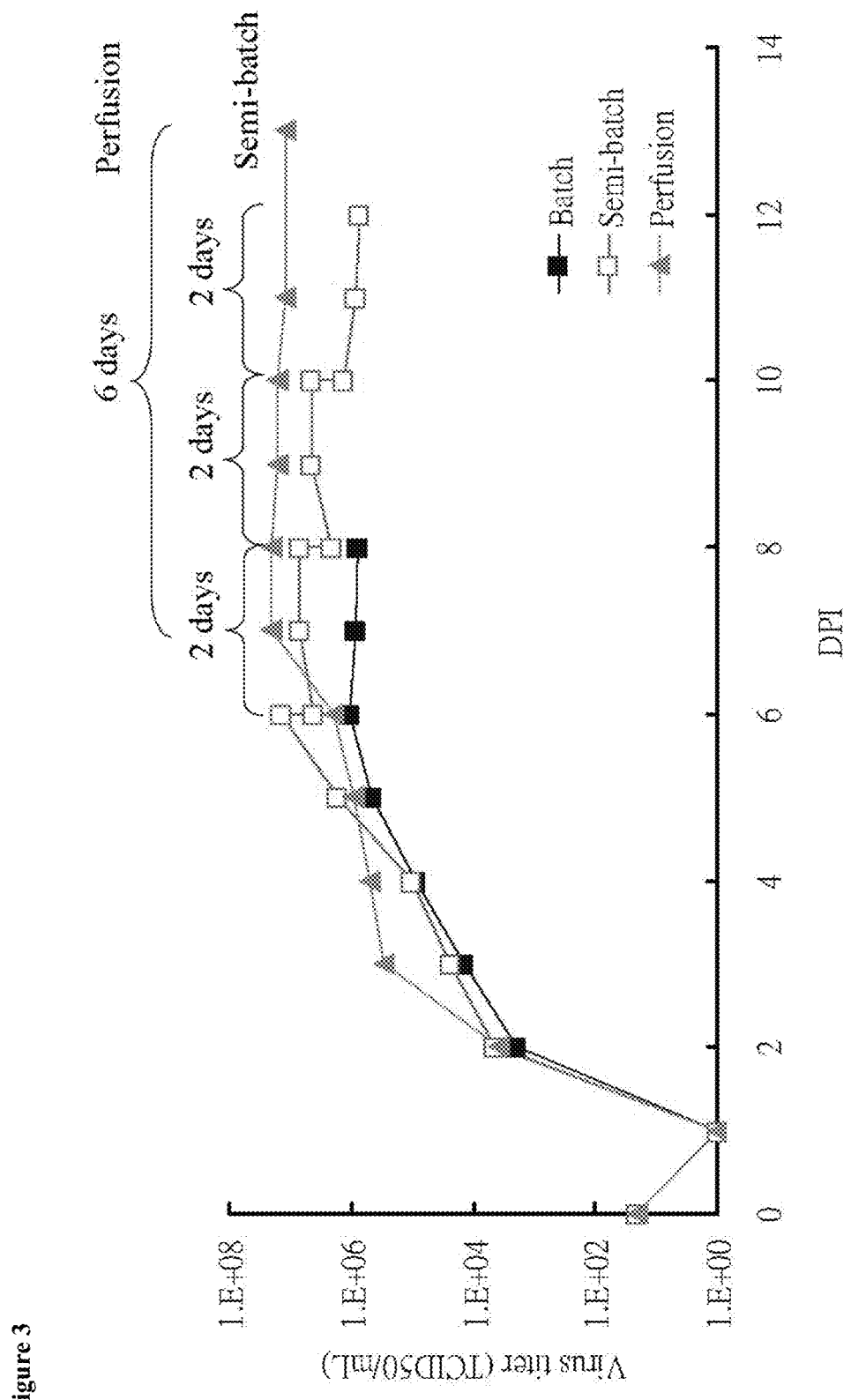
FIG. 3 is a diagram showing production of EV71-E59 viral stocks in a 5.0 L bioreactor.
Figure 4A:
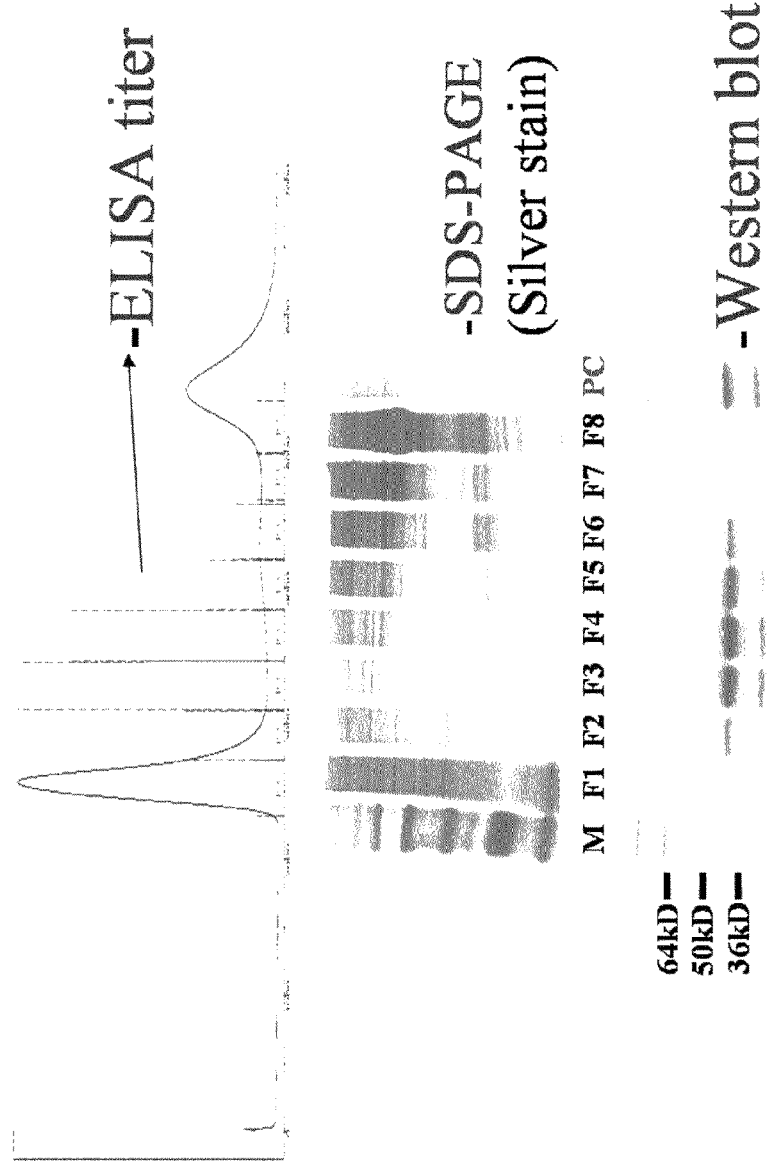
FIGS. 4A-4C are diagrams and photographs showing purification of an EV71-E59 viral stock by liquid chromatography.
Figure 4B:
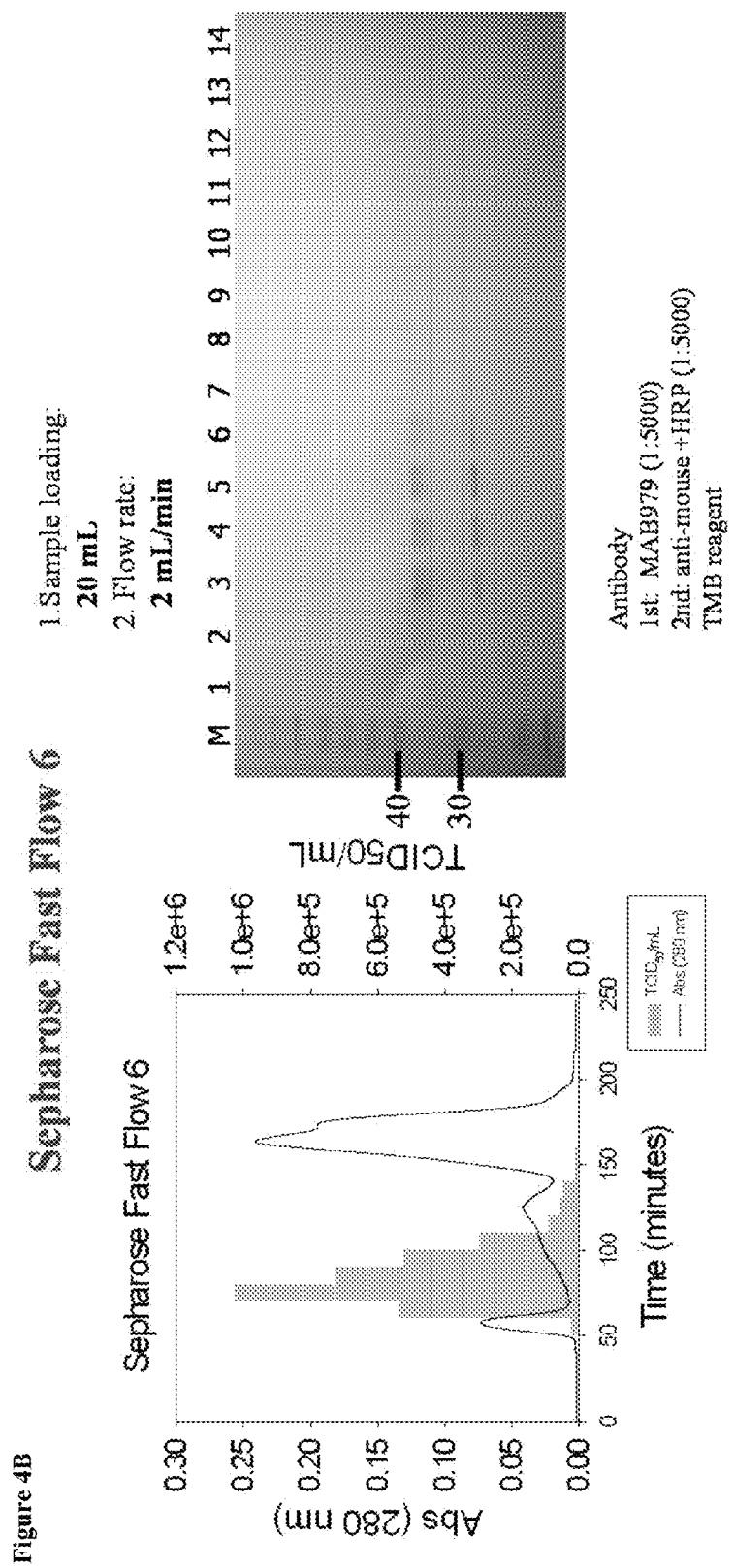
Figure 4C:
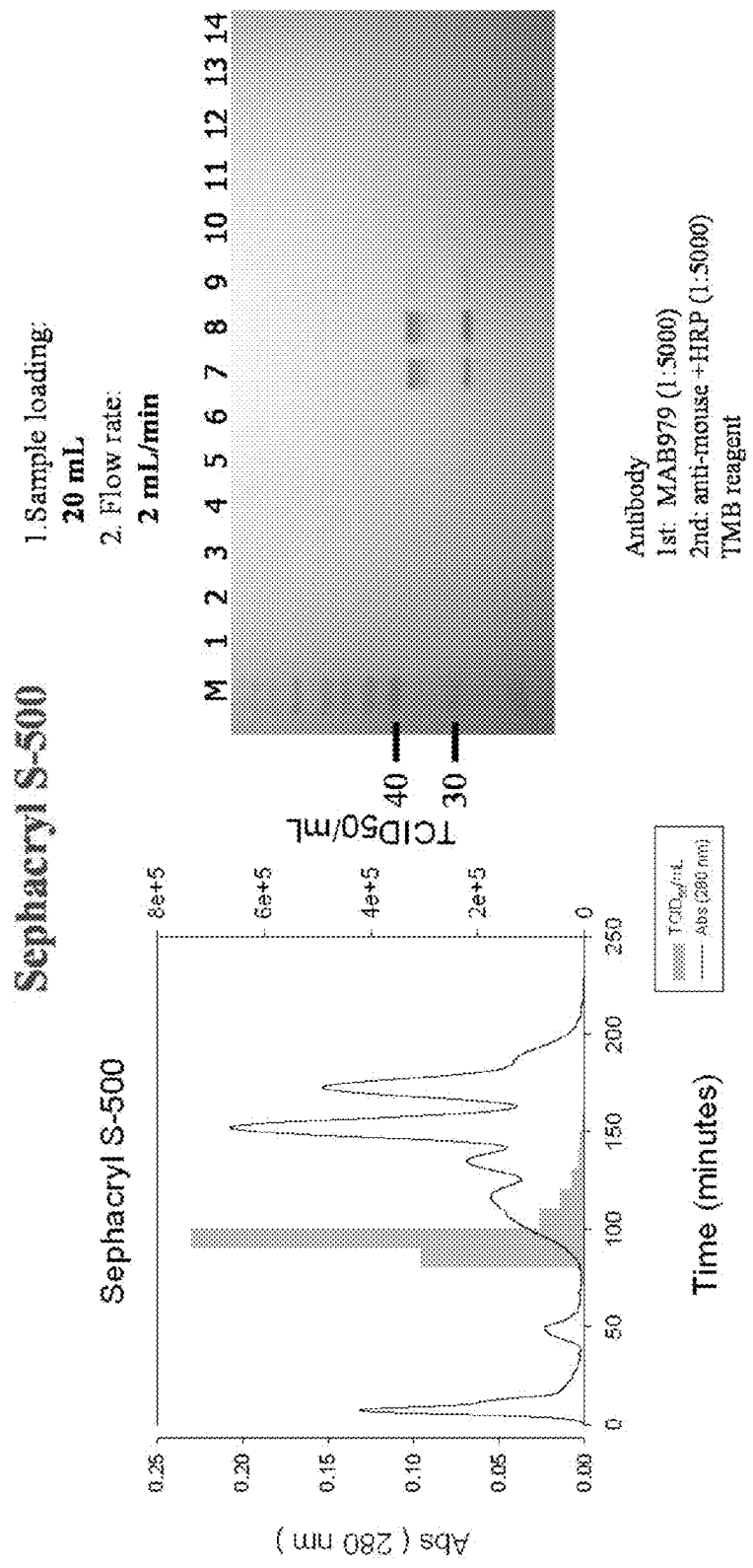
Figure 5:
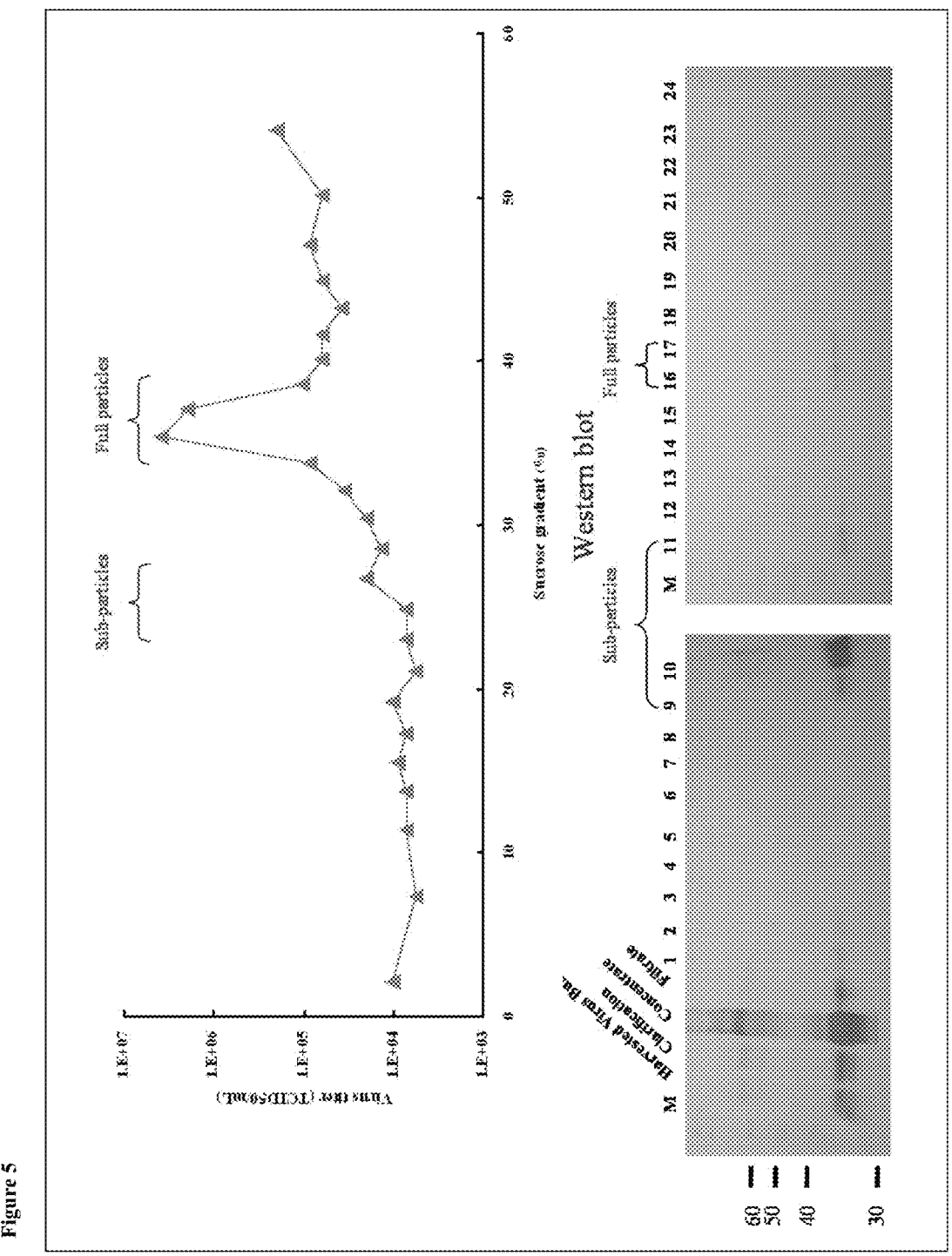
FIG. 5 is a set of a diagram and photographs showing purification of an EV71-E59 viral stock by continuous sucrose gradient ultracentrifugation.
Figure 6:
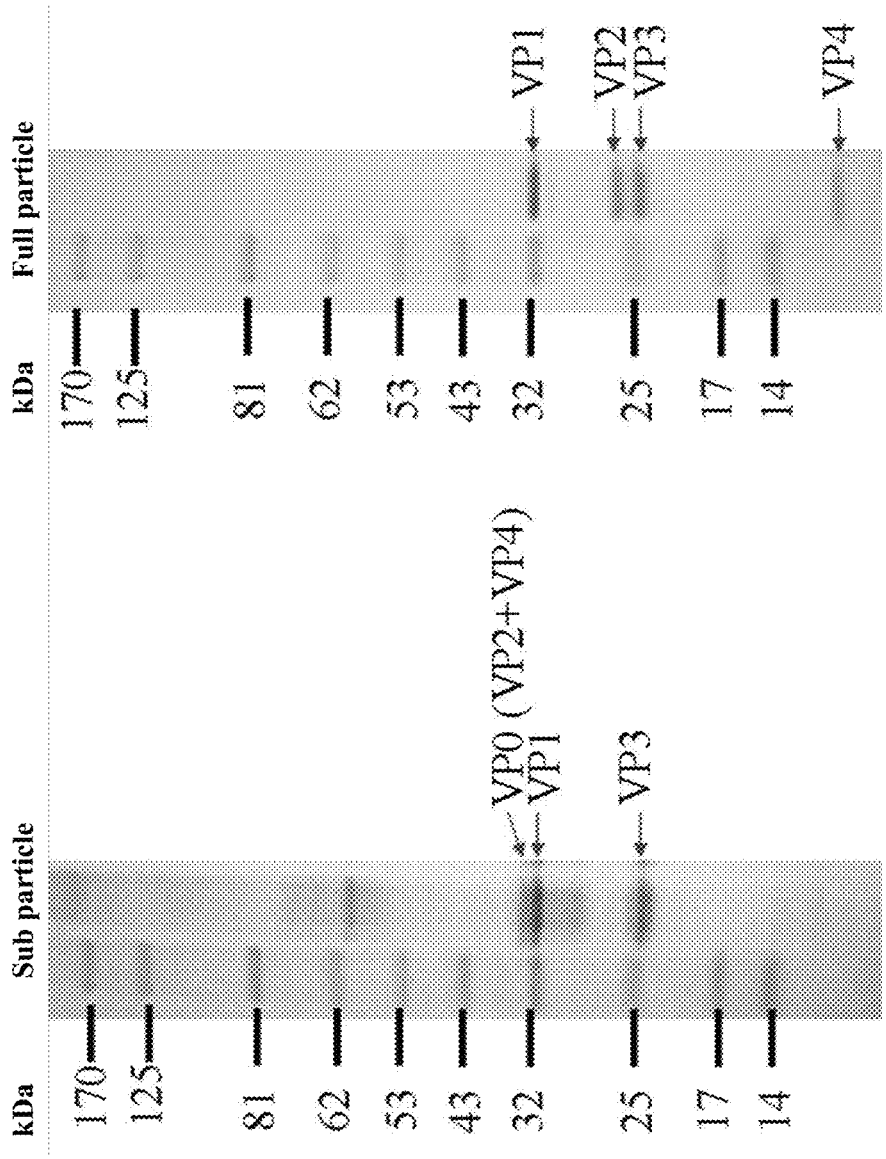
FIG. 6 is a set of photographs showing characteristics of EV71-E59 virions.
Figure 7:
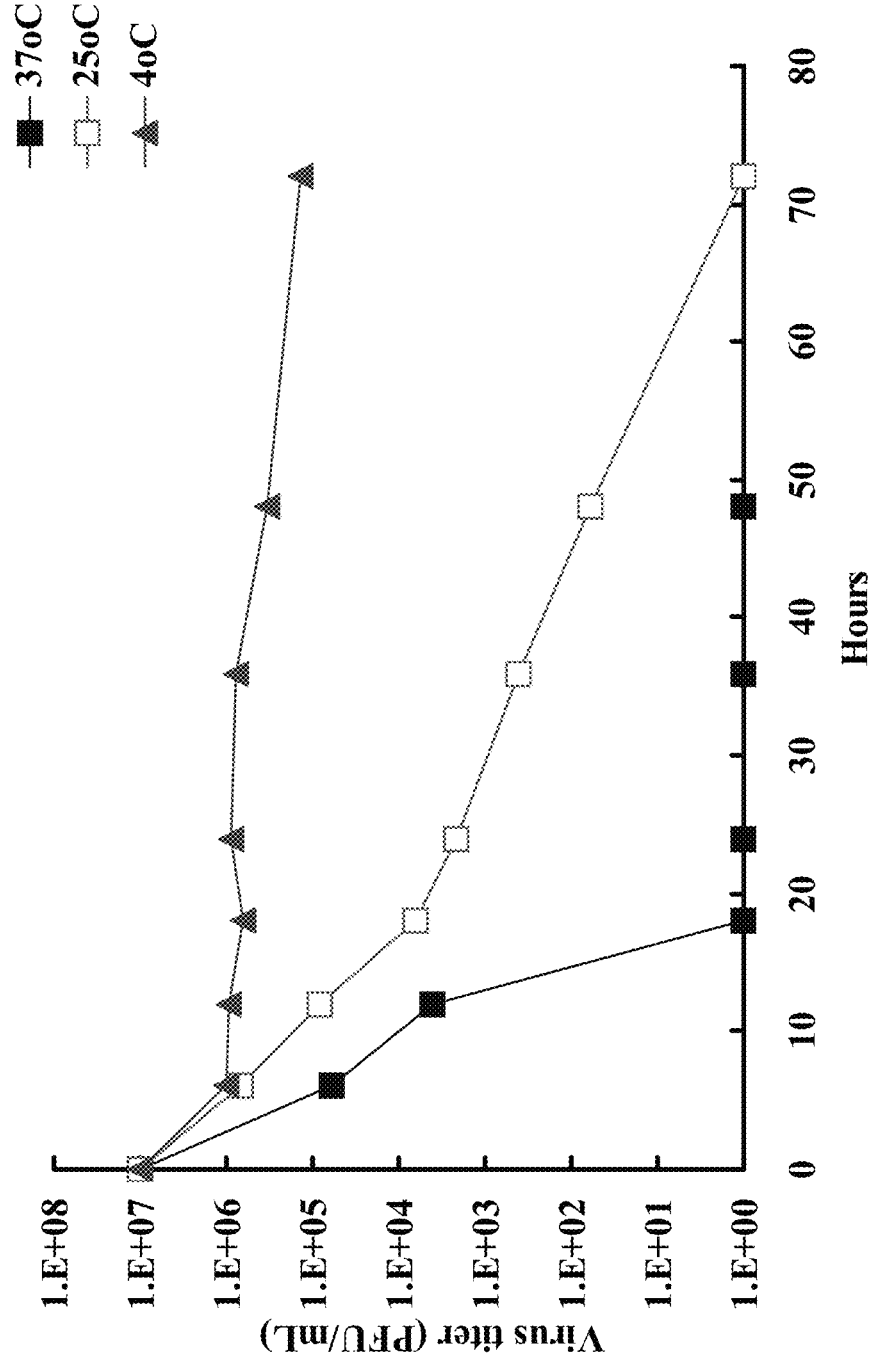
FIG. 7 is a diagram showing inactivation kinetics of the EV71-E59 virus.
Figure 8:
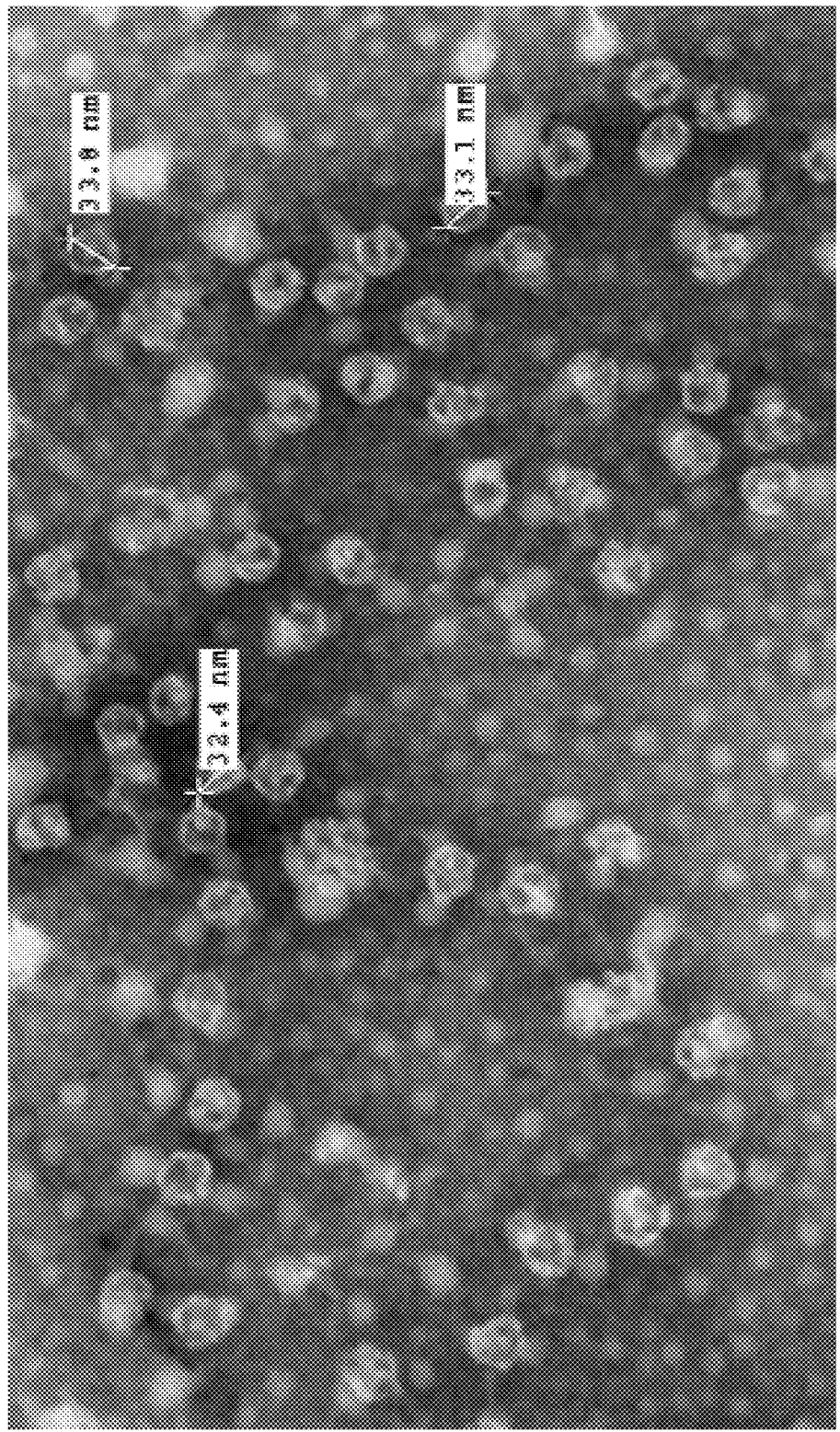
FIG. 8 is a photograph showing detection of EV71-E59 virions by TEM.

This invention is based, at least in part, on the unexpected discoveries of EV71 antigens that can elicit immune responses and related methods. EV71 is a non-enveloped RNA virus of the family Picornaviridae, genus *Enterovirus*. The characteristics of this family include the fact that these viruses are nonenveloped, icosahedral symmetry, 30±5 nm in diameter, contain a single molecule of plus sense ssRNA (7.5-8.5 kb), and that they replicate in the cytoplasm. The viral capsid is icosahedral (T=1) in symmetry and is composed of 60 identical units each consisting of four structural proteins: VP1, VP2, VP3 and VP4. EV71 virus first was isolated in 1969 in the United States. The complete nucleotide sequence of the EV71 prototype strain BrCr has been determined.

As described herein, this invention features a method of producing a purified EV71 virus antigen. The method involves culturing host cells that produce EV71 virus. Various culturing methods can be used. Examples includes methods based on roller bottles, microcarrier-bioreactors, spinners, and Beads-to-Beads transfer.

Various cells can be used as hosts to produce the above-described EV71 antigen. In one example, Vero cells are used. Vero cell is a regulatory-accepted cell line for human vaccine production and have been used to produce human polio and rabies vaccines. Since Vero cells are anchorage-dependent, microcarrier technology can be used for establishing a large-scale cell culture process for vaccine production. To that end, microcarrier technology and serum-free culture can be used to overcome the drawbacks of culturing using high serum-protein content, including complicating downstream purification process and the risk of prion contamination. In a preferred embodiment, a VP-SFM medium (GIBCO) is preferred. Other media, such as Plus Vero (CESCO), Excell (SAFC), and HyQ (HYCLONE), can also be used.

To produce viral antigens, the host cells generally can be infected at MOI of $10^{-2}$ to $10^{-6}$, e.g., about $10^{-5}$. For collection, batch, semi-batch, or perfusion techniques can be used. To purify vial antigens, one can use liquid chromatography (LC) or sucrose gradient ultracentrifuge purification. Virus inactivation can be carried out using, e.g., 4000:1 37% formalin at 25° C. to 37° C. To evaluate potency of antigen thus obtained and of vaccines containing the antigen, one can use the cross-neutralization epitope in VP2 antigen (e.g., one of SEQ ID NOs: 1-4, 8-10, 25-29, 31-32, 34-35, and 38) as the biomarker for vaccine potency test.

The invention features an immunogenic composition, such as a vaccine, against virus infection and/or related other disorders, including hand, foot and mouth disease, and associated neurological diseases. As mentioned above, the immunogenic composition contains an antigen, e.g., an EV71 virus full-particle, an EV71 virus sub-particle, or a polypeptide.

An "antigen" refers to a particle or a molecule containing one or more epitopes that will stimulate a host's immune system to make a humoral and/or cellular antigen-specific response. The term "antigen" is used interchangeably with "immunogen." As a result of coming in contact with appropriate cells, an antigen induces a state of sensitivity or immune responsiveness and reacts in a demonstrable way with antibodies or immune cells of the sensitized subject in vivo or in vitro. An antigen can be specifically recognized and bound by antibodies in an organism. An antigen in association with a major histocompatibility complex (MHC) can also be recognized and bound by receptors on the surface of T lymphocytes (T-cells), leading to the activation of the T-cells. The term "epitope" as used herein refers to the site on an antigen to which a specific antibody molecule or a T-cell receptor binds. The term is used herein interchangeably with "antigenic determinant" or "antigenic determinant site."

The term "immune response" or "immunogenic response" refers to any reaction of the immune system in response to an antigen in a subject. Examples of an immune response in a vertebrate include, but are not limited to, antibody production, induction of cell-mediated immunity, and complement activation. The immune response to a subsequent stimulus by the same antigen, also named the secondary immune response, is more rapid than in the case of the primary immune response. The term "immunogenic" refers to a capability of producing an immune response in a host animal against an antigen or antigens. This immune response forms the basis of the protective immunity elicited by a vaccine against a specific infectious organism.

An "antibody" refers to an immunoglobulin molecule or at least one immunologically active portion of an immunoglobulin molecule that has a specific amino acid sequence and binds only to an antigen or a group of antigens that are closely related. Examples of antibodies include IgG, IgM, IgA, IgD and IgE. Examples of immunologically active portions of immunoglobulin molecules include Fab and F(ab)'2 fragments which can be generated by treating the antibody with an enzyme such as pepsin. An antibody can be a monoclonal antibody or a polyclonal antibody. A "monoclonal antibody" refers to a population of antibody molecules that contains only one species of an antigen binding site and that is capable of immunoreacting with a particular epitope. A "polyclonal antibody" refers to a population of antibody molecules that contains more than one species of antigen binding sites and that is capable of immunoreacting with more than one epitope on the polypeptide.

Preferably, the antigen can be expressed and isolated from host cells or their culture medium. Their identity and purity can be confirmed via methods known in the art, e.g., immunoblotting with antibody or mass spectrometry. An antigen thus prepared can be used to prepare an immunogenic composition (e.g., a vaccine) for generating antibodies and immune response against EV71 virus in a subject (e.g., a human subject) susceptible to the virus. Such compositions can be prepared, e.g., in the manners described below, or by any other equivalent methods known in the art.

This antigen can be mixed with a pharmaceutically acceptable carrier such as a phosphate buffered saline, a bicarbonate solution, or an adjuvant to produce a pharmaceutical composition. The carrier must be "acceptable" in the sense that it is compatible with the active ingredient of the composition, and preferably, capable of stabilizing the active ingredient and not deleterious to the subject to be treated. The carrier is selected on the basis of the mode and route of administration, and standard pharmaceutical practice. Suitable pharmaceutical carriers and diluents, as well as pharmaceutical necessities for their use, are described in Remington's Pharmaceutical Sciences. In one example, the antigen is mixed with an adjuvant to form a composition useful for immune modulation. This composition may be prepared as injectables, as liquid solutions or emulsions. See U.S. Pat. Nos. 4,601,903; 4,599,231; 4,599,230; and 4,596,792.

An "adjuvant" refers to a substance added to an immunogenic composition, such as a vaccine, that while not having any specific antigenic effect in itself, can stimulate the immune system and increase the immune response to the immunogenic composition. Examples of adjuvants include, but are not limited to, alum-precipitate, Freund's complete adjuvant, Freund's incomplete adjuvant, monophosphoryl-lipid A/trehalose dicorynomycolate adjuvant, water in oil emulsion containing Corynebacterium parvum and tRNA, and other substances that accomplish the task of increasing immune response by mimicking specific sets of evolutionarily conserved molecules including liposomes, lipopolysaccharide (LPS), molecular cages for antigen, components of bacterial cell walls, and endocytosed nucleic acids such as double-stranded RNA, single-stranded DNA, and unmethylated CpG dinucleotide-containing DNA. Other examples include cholera toxin, *E. coli* heat-labile enterotoxin, liposome, immune-stimulating complex (ISCOM), immunostimulatory sequences oligodeoxynucleotide, and aluminum hydroxide. The composition can also include a polymer that facilitates in vivo delivery. See Audran et al. Vaccine 21:1250-5, 2003; and Denis-Mize et al. Cell Immunol., 225:12-20, 2003. Alternatively, the antigen described herein can be used in a vaccine without any adjuvant.

An effective amount of the composition described above may be administered parenterally, e.g., subcutaneous injection or intramuscular injection. Alternatively, other modes of administration including suppositories and oral formulations may be desirable. For suppositories, binders and carriers may include, for example, polyalkalene glycols or triglycerides. Oral formulations may include normally employed incipients such as pharmaceutical grades of saccharine, cellulose, magnesium carbonate and the like. These compositions take the form of solutions, suspensions, tablets, pills, capsules, sustained release formulations or powders. An "effective amount" means that amount of a composition that elicits a biological or medicinal response in a tissue system of a subject, or in a subject, that is being sought by a researcher, veterinarian, doctor or other clinician.

A vaccine can be administered in a manner compatible with the dosage formulation, and in an amount that is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the polypeptide of this invention. Suitable regimes for initial administration and booster doses are also variable, but may include an initial administration followed by subsequent administrations. The dosage of the vaccine may also depend on the route of administration and varies according to the size of the host.

A subject susceptible to virus infection (especially young children) can be identified by methods known in the art and administered a composition of the invention. The dose of the composition depends, for example, on the particular antigen, whether an adjuvant is co-administered, and the type of adjuvant co-administered, the mode and frequency of administration, as can be determined by one skilled in the art. Administration is repeated as necessary, as can be determined by one skilled in the art. For example, a priming dose can be followed by three booster doses at weekly intervals. A booster shot can be given at 4 to 8 weeks after the first immunization, and a second booster can be given at 8 to 12 weeks, using the same formulation. Sera or T-cells can be taken from the subject for testing the immune response elicited by the composition against the virus. Methods of assaying antibodies or cytotoxic T cells against a protein or infection are well known in the art. Additional boosters can be given as needed. By varying the amount of polypeptide/protein, the dose of the composition, and frequency of administration, the immunization protocol can be optimized for eliciting a maximal immune response. Before a large scale administering, efficacy testing is desirable. In an efficacy testing, a non-human subject (e.g., mouse, rat, rabbit, house, pig, cow, or monkey) can be administered via an oral or parenteral route with a composition of the invention. After the initial administration or after optional booster administration, both the test subject and the control subject (receiving mock administration) can be challenged with virus to test the efficacy of the composition.

The invention also features an isolated antibody that selectively binds to a peptide having one of the sequences mentioned above. Also featured is a method of producing the antibody by immunizing an animal with the above-described immunogenic composition, which elicits an immune response in the animal to produce the antibody; and isolating the antibody or a cell producing the antibody from the animal.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

Materials and Methods

1. Cell, culture medium, and virus

Vero cells (green monkey kidney cells) were obtained from the American Type Culture Collection (ATCC). The Vero cells were grown in a VP-SFM medium (GIBCO) and passaged twice weekly in T-flasks. An EV71 strain, EV71-E59, was obtained from the Center of Disease Control, Taipei, Taiwan. EV71-E59 viral stocks were harvested from the culture media of the infected Vero cells on $3^{rd}$ day post infection (DPI). The viral stocks were stored at $-80°$ C.

2. Production of an EV71-E59 viral stock in a roller bottle

In a roller bottle culture, Vero cells were passaged in an 850 $cm^2$ roller bottle (CORNING) with 200 mL of a VP-SFM medium that was stirred at a rate of 0.33 rpm in a roller rack at $37°$ C. The inoculating cell density in the roller bottle culture was about $1.5-2\times10^7$ cells and the cell density reached $1.5-2\times10^8$ cells following 6 days of cultivation. After a 100% culture medium replacement, the Vero cells were infected with the EV71-E59 virus at MOI of $10^{-5}$. Two hundred or four hundred milliliter-working volumes of the medium were tested in this study. EV71-E59 viral stocks were harvested from the culture media on the $5^{th}$ DPI.

3. Production of EV71-E59 viral stocks in bioreactors

EV71-E59 viral production was carried out according to the microcarrier cell culture process described in Wu et al. 2004 Vaccine 22(29-30):3858-64.

A BIOFLO 310 bioreactor (NBS, US) was used in the microcarrier culture process. The bioreactor cultures (1.4 L and 5 L of working volumes) were stirred at a rate of 60 rpm at pH 7, and dissolved oxygen (DO) content was controlled at 50% by a gas mixer apparatus. Vero cells used in the bioreactor were first harvested from the above-described roller bottle. Cytodex 1 microcarriers (GE) were prepared following the manufacture's instructions. The Cytodex 1 microcarriers were immersed in a phosphate buffer saline (PBS) for more than three hours and autoclaved for 15 min prior to setting up each experiment. The autoclaved microcarriers were washed twice with a VP-SFM medium. The inoculating cell density in the bioreactor culture was about $2\times10^5$ cells/mL. On day 3, 70% of the culture medium was replaced with a fresh medium and on day 6, the cell density reached $2-2.5\times10^6$ cells/mL. After a 70% culture medium replacement, the Vero cells were infected with the EV71-E59 virus at MOI of $10^{-5}$. In one example, the EV71-E59 virus was harvested from the microcarrier culture medium on $6^{th}$ DPI. In another example, a semi-batch culture method was used for harvesting the virus by replacing 70% of the culture medium every two days on $6^{th}$, $8^{th}$, $10^{th}$ and $12^{th}$ DPI. In yet another example, a perfusion culture method was used for harvesting the virus by replacing 50-70% of the medium every day on $6^{th}$ to $13^{th}$ DPI.

4. Purification of EV71-E59 viral stocks by liquid chromatography

After harvesting EV71-E59 viral stocks in the manner described above, debris of Vero cells was removed by a 0.65 µm filter (SARTORS), and the viral stocks were concentrated and diafiltrated using a 100K TFF cassette (PALL). The concentrated viral stocks were loaded to a Sepharose Fast Flow 6 gel column for liquid chromatography using a FPLC system, AKTA pilot (GE HEALTHCARE). A Sephacryl S-500 gel column was also used to carry out the purification process. These resultant fractions were subjected to SDS-PAGE and Western analyses to detect EV71 viruses using an MAB979 antibody (MILLIPORE). The purified EV71-E59 viral stocks were concentrated using a 100K TFF cassette (PALL) and re-suspended in PBS. The total protein concentration of the re-suspended viral stock was determined using a BCA protein assay (PIERCE).

5. Purification of EV71-E59 viral stocks by continuous sucrose gradient ultracentrifugation After harvesting EV71-E59 viral stocks in the manner described above, debris of Vero cells was removed by a 0.65 µm filter (SARTORS), and EV71-E59 viral stocks were concentrated using a 100K TFF capsule (PALL). The concentrated viral stocks were loaded to a 10-50% continuous sucrose gradient for ultracentrifugation at 32,000 RPM for 3 hours. These resultant fractions were subjected to SDS-PAGE and Western analyses to detect purified EV71 viruses by an MAB979 antibody (MILLIPORE). The purified EV71-E59 viral stocks were diafiltrated using an Amicon 100K tube (MILLIPORE) by centrifuging at 3,000×g. The concentrated stock was re-suspended in PBS. The total protein concentration of the re-suspended viral stock was determined using a BCA protein assay (PIERCE).

6. Determination of viral titers

Viral titers were determined from the median end point of the tissue culture's infectious dose ($TCID_{50}$). Serially diluted viral samples (from $10^{-1}$ to $10^{-8}$) were added to Vero cells in 96-well plates and 10-replicates were examined for each dilution. The 96-well plates were incubated for six days at 37° C., and the $TCID_{50}$ values were obtained by counting the cytopathic effects of the infected Vero cells. The $TCID_{50}$ values were calculated using the Reed-Muench methods.

7. Preparation of an inactivated EV71-E59 virus and immunization of animals

An EV71-E59 viral stock was mixed with a 37% formaldehyde solution (MERCK) at a volume ratio of 4000:1 ratio and incubated at 37° C. over 3 days to inactivate the EV71-E59 virus. The inactivated viral stock was absorbed on aluminum phosphate at room temperature for 3 hours before immunization. A group of 6 female BALB/c mice (18-25 g, 6-8 weeks after birth) were immunized intramuscularly (i.m.) with 0.2 mL of the alum-absorbed inactivated EV71-E59 viral stock, and the same doses were used to boost the mice two weeks after the first immunization. Two New Zealand white rabbits were also immunized and after 2 to 3 weeks boosted i.m. with 0.5 mL of the alum-absorbed inactivated EV71-E59 viral stock. Likewise, a rhesus monkey was immunized i.m., and after 1 month boosted i.m. with 0.5 mL of the alum-absorbed inactivated EV71-E59 viral stock. The immunized animals were bled one week after the boost, and the sera collected for analysis of viral neutralization.

8. Detection of EV71-E59 virions by transmission electron microscopy (TEM)

An inactivated EV71-E59 viral stock was dropped on a formvar-coated and carbon-vaporized 200-mesh copper grid. The sample (20 µL) was kept on the copper grid for 15 min at room temperature, and then the excess sample was removed with a piece of filter paper. After being washed with $ddH_2O$ once, the copper grid was stained with a 2% phosphotungustic acid solution for 2 min and the solution was subsequently removed with a piece of filter paper. The stained grid was dried for more than 3 days. The grid was observed under a Hitachi H-7650 electron microscope.

9. Neutralizing assays for anti-EV71-E59 sera

The sera collected from immunized mice were inactivated at 56° C. for 30 min. Each serum sample was added to a microtube and diluted in a two-fold serial dilution using a fresh VP-SFM medium. A suspension with 200 $TCID_{50}$ of the EV71-E59 virus in a volume of 400 4 µL was added to each tube that contains 400 µL serially-diluted sera. After being incubated at 4° C. for 18-24 hours, 100 µl of serially-diluted samples were added to Vero cells in 96-well plates. The cultures in 96-well plates were incubated for seven days at 37° C., and the $TCID_{50}$ values were obtained by counting the cytopathic effects in the infected Vero cells. The 50% neutralization inhibition dose ($ID_{50}$) that is the geometric reciprocal of the serum dilution yielding 50% reduction in the viral titer was obtained using the Reed-Muench methods.

10. Design and synthesis of synthetic peptides

The overlapping synthetic peptides of the EV71 strain TW/2086/98 VP1, VP2 and VP3 capsid proteins were synthesized at Kelowna International Scientific Inc. (Taipei Hsien, Taiwan), including a set of 57 overlapping synthetic peptides spanning the entire sequence of the VP1 capsid protein, a set of 49 overlapping synthetic peptides spanning the entire sequence of the VP2 capsid protein, and a set of 47 overlapping synthetic peptides spanning the entire sequence of the VP3 capsid protein. Each peptide contains 15 amino acid residues with 10 residues overlapping with the adjacent peptides.

11. Detection of antibodies by ELISA

The affinity of an antibody to each synthetic peptide was measured by enzyme-linked immunosorbent assay (ELISA). Each well of a 96-well plate (COSTAR EIA) was coated at 4° C. overnight with 50 µL of an individual synthetic peptide or purified virus that was diluted to 10 µg/mL in a coating buffer (0.1M $NaHCO_3$, pH=9.5). An inactivated EV71-E59 viral stock, 0.5 µg/well, was used as a positive control. A duplicated well was set up for each synthetic peptide or purified virus. After being washed once with 1×PBST (phosphate buffer saline containing 0.05% Tween 20), each well was blocked with 200 µL of a blocking buffer (5% non-fat milk in PBS) and incubated for 2 hours at room temperature. A primary antibody 1:200-diluted in 1% BSA/PBS was added to each well (100 µL per well) and incubated for 2 hours. After removing the primary antibody solution, the wells were washed six times with 1×PBST. To each of the washed wells, 100 µL of a secondary antibody conjugated with Horseradish Peroxidase, 1:5000-diluted in 1% BSA/PBS, was added and incubated for 2 hours. Upon removing the secondary antibody solution, the wells were washed six times with 1×PBST. A reaction was developed by adding a TMB substrate solution (KPL) and incubating at room temperature for 15 minutes. The reaction was stopped by adding $H_2SO_4$ (1N) and the absorbance was measured at 450 nm by an ELISA reader.

12. Sequence alignment and prediction of structural homology

All related EV71 strains were searched from the NCBI PubMed website (www.ncbi.nlm.nih.gov/pubmed/). The genomic sequences of EV71 VP2 proteins were aligned using computer software called ClustalW2 (www.ebi.ac.uk/Tools/clustalw2/index.html).

Results

1. Production of an EV71-E59 viral stock in a roller bottle

Vero cells were grown in an 850 cm² roller bottle with 200 mL of a VP-SFM medium at 37° C. When the cell density reached 1.5-2×10⁸ cells, the culture medium was replaced and the Vero cells were infected with the EV71-E59 virus at MOI of 10⁻⁵. As shown in FIG. 1, the viral titer reached 2-4.5×10⁶ $TCID_{50}$/mL on $3^{rd}$ DPI and the viral titer maintained stable yields. The production kinetics of the EV71-E59 virus was similar when either 200 mL or 400 mL of the culture medium was used.

2. Production of EV71-E59 viral stocks in bioreactors

A microcarrier cell culture in a VP-SFM medium was used for producing EV71-E59 viral stocks. Vero cells were grown on Cytodex 1 microcarriers at a carrier concentration of 5 g/L at 37° C. in a batch, semi-batch, or perfusion bioreactor. When the cell density reached 2-2.5×$10^6$ cells/mL, 70% of the culture medium was replaced with a fresh VP-SFM medium and the Vero cells were infected with the EV71-E59 virus at MOI of $10^{\times 5}$ in the bioreactor at 32° C. It was found that the maximal viral titer was 2.7×$10^5$ $TCID_{50}$/mL on $6^{th}$ DPI in a 1.4 L-batch bioreactor culture. The viral titers ranged from 0.8 to 7×$10^6$ $TCID_{50}$/mL on $6^{th}$ to $12^{th}$ DPI in a 1.4 L semi-batch bioreactor culture. The viral titers ranged from 0.5 to 2×$10^6$ $TCID_{50}$/mL on $6^{th}$ to $12^{th}$ DPI in a 1.4 L perfusion bioreactor culture (FIG. 2). The maximal viral titer was 1×$10^6$ $TCID_{50}$/mL on $6^{th}$ DPI in a 5 L-batch bioreactor culture. The viral titers ranged from 0.7 to 13×$10^6$ $TCID_{50}$/mL on $6^{th}$ to $12^{th}$ DPI in a 5 L semi-batch bioreactor culture. The viral titers ranged from 1 to 2×$10^7$ $TCID_{50}$/mL on $7^{th}$ to $13^{th}$ DPI in a 5 L perfusion bioreactor culture (FIG. 3). The semi-batch and perfusion culture methods could increase harvesting yields by 3-5 folds in comparison to the batch culture method.

3. Purification of an EV71-E59 viral stock by liquid chromatography

A concentrated EV71-E59 viral stock (20 mL) was loaded to a Sepharose Fast Flow 6 gel column or Sephacryl S-500, and subjected to liquid chromatography. The EV71-E59 virus was collected mainly in fractions 3 and 4 based on Western analysis (FIGS. 4A and 4B). Alternatively, the concentrated viral stock (20 mL) was loaded to a Sephacryl S-500 gel column. The main fractions of the EV71-E59 virus were found in fractions 7 and 8 (FIG. 4C). The pooled fractions were concentrated. The purified viral stocks were diafiltrated and re-suspended with PBS.

4. Purification of an EV71-E59 viral stock by continuous sucrose gradient ultracentrifugation The concentrated EV71-E59 viral stocks were loaded to a 10-50% continuous sucrose gradient for ultracentrifugation at 32,000 RPM for 3 hours. When the EV71-E59 virus was isolated from a culture medium, two kinds of EV71-E59 virions were detected by Western analysis (FIG. 5). EV71-E59 sub-particles were detected in fractions having 25 to 28% sucrose, while EV71-E59 full-particles were detected in fractions having 35 to 38% sucrose. The EV71-E59 full-particle was more infectious than the EV71-E59 sub-particle. These two kinds of EV71-E59 viral particles were separately diafiltrated and re-suspended with PBS.

5. Characteristics of EV71 virions

Ultra pure EV71-E59 viral stocks were obtained by combining purifications with liquid chromatography and sucrose gradient ultracentrifugation. The samples were loaded onto a 10% SDS-polyacrylamide gel and stained by Coomassie Blue. EV71-E59 sub- and full-particles exhibited different patterns (FIG. 6). The predicted and observed molecular weights of EV71-E59 viral antigens were listed in Tables 1A-1C.

TABLE 1A

Completely processed viral antigens

| EV71-E59 | Amino acid | Residues | Predicted MWa | Observed MWb |
|---|---|---|---|---|
| VP4 | 1-69 | 69 | 7.49 | 8 |
| VP2 | 70-323 | 254 | 27.78 | 28 |
| VP3 | 324-565 | 242 | 26.52 | 27 |
| VP1 | 566-862 | 297 | 32.73 | 36 |

TABLE 1B

Incompletely processed viral polypeptides

| EV71-E59 antigens | Amino acid sequences | Residues | Predicted MWa (kDa) | Observed MWb (kDa) |
|---|---|---|---|---|
| VP0 (VP4 + VP2) | 1-323 | 323 | 35.27 | 38 |
| VP3 + VP1 | 324-862 | 519 | 59.25 | 62 |

TABLE 1C

Viral antigens cross-linked by formaldehyde

| EV71-E59 antigens | Amino acid sequences | Residues | Predicted MWa (kDa) | Observed MWb (kDa) |
|---|---|---|---|---|
| VP4 + VP2 | 1-323 | 323 | 35.27 | 38 |
| VP4 + VP2 + VP4 | | | 42.76 | 45 |
| VP3 + VP1 | 324-862 | 519 | 59.25 | 62 |
| VP4 + VP2 + VP3 + VP1 | 1-862 | 519 | 94.52 | 98 |

As shown in FIG. 6, an EV71-E59 sub-particle had more antigens, mainly including VP0 (VP2+VP4), VP1, and VP3. An EV71-E59 full-particle only had the basic viral components: VP1, VP2, VP3, and VP4.

6. Preparation of an inactivated EV71-E59 viral stock

An EV71-E59 viral stock (1×$10^7$ PFU/mL) was mixed with a 37% formaldehyde solution at a volume ratio of 4000:1 and incubated at 37° C., 25° C. or 4° C. for viral inactivation. In 24 hours, the EV71-E59 virus was inactivated at 37° C., while 3 days were needed to inactivate the EV71-E59 virus at 25° C. (FIG. 7). In 3 days, the EV71-E59 viral titer was still high if the virus was subjected to inactivation at 4° C. It was found that raising temperature significantly increased the inactivation rate. It took 2.16 days to reduce the EV71-E59 viral titer to $10^{-12}$ PFU/mL at 37° C. (Table 2).

TABLE 2

Inactivation time of the EV71-E59 virus

| Viral titer (TCID50/mL) | 37° C. | 25° C. | 4° C. |
|---|---|---|---|
| $10^{-8}$ | 1.71 d | 6.45 d | 24.90 d |
| $10^{-12}$ | 2.16 d | 8.27 d | 31.64 d |

To ensure the safety of vaccination, inactivation of the EV71-E59 virus was performed at 37° C. for 5-6 days.

7. Detection of EV71-E59 virions by TEM

An inactivated EV71-E59 stock was stained with a 2% phosphotungustic acid solution and observed under a transmission electron microscope. It was found that the EV71-E59 virus still maintained as a whole viral particle after inactivation. The sizes of EV71-E59 viral particles ranged from 30 to 35 nm in diameters (FIG. 8). Both sub- and full-particle samples were detected having whole viral particles.

8. Immunogenicity study of an inactivated EV71-E59 virus

To further determine the immunogenicity of the EV71-E59 virus, purified viral stocks from liquid chromatography and from continuous sucrose gradient ultracentrifugation were treated with a formaldehyde solution for viral inactivation. Mice, rabbits, and monkeys were immunized with the inactivated EV71-E59 virus absorbed on aluminum phosphate following a two-week immunization schedule. In a mouse model, the results revealed that the inactivated EV71-E59 virus prepared from liquid chromatography and subsequently from continuous sucrose gradient ultracentrifugation elicited a notable titer of neutralizing antibodies (Table 3).

TABLE 3

Immunogenicity of the inactivated EV71-E59 virus in a mouse model.

| Purification method | Sample | Total protein (μg/dose) | Neutralization antibody (TCID50) |
|---|---|---|---|
| Liquid Chromatography | Mix particles | 0.2 | 100 |
| Liquid Chromatography | Mix particles | 1 | 854 |
| Liquid Chromatography | Mix particles | 2 | 911 |
| Sucrose gradient ultra-centrifuge | Sub-particles | 2.5 | 1218 |
| Sucrose gradient ultra-centrifuge | Full-particles | 2.5 | 2699 |

An EV71-E59 full-particle elicited a higher titer of neutralizing antibodies than a sub-particle using same immunization schedule. In rabbit and monkey models, the inactivated EV71-E59 virus prepared from a viral stock which had been purified with liquid chromatography also induced higher neutralizing titers (Table 4 and Table 5).

TABLE 4

Immunogenicity of inactivated EV71-E59 virus in a rabbit model.

| | Purification method | Sample | Total protein (μg/dose) | Neutralization antibody (TCID50) |
|---|---|---|---|---|
| Rabbit-1 | Liquid Chromatography | Mix particles | 10 | 13573 |
| Rabbit-2 | Liquid Chromatography | Mix particles | 10 | 19308 |

TABLE 5

Immunogenicity of inactivated EV71-E59 virus in a monkey model.

| Purification method | Sample | $1^{st}$ dosage (μg/dose) | $2^{nd}$ dosage (μg/dose) | Neutralization antibody (TCID50) |
|---|---|---|---|---|
| Liquid Chromatography | Mix particles | 20 | 10 | >1659 |

These antisera were used to perform a cross-neutralization assay, and the results shown that these antisera were against the C5 and B5 subgenotypes of EV71 viruses (Table 6). Table 6. Neutralizating antibody titers of different sera against genogroups C5 and B5 of EV71 viruses.

TABLE 6

| | B4 sub-genotype | C5 sub-genotype | B5 sub-genotype |
|---|---|---|---|
| Mouse/E59 (B4) | 854 | 8 | 31 |
| Rabbit-1/E59 (B4) | 13573 | 13520 | ≥16384 |
| Rabbit-2/E59 (B4) | 19308 | ≥16384 | ≥16384 |
| Monkey/E59 (B4) | >1659 | 5623 | 3169 |

Noticeably, the chemically inactivated EV71-E59 virus also induced neutralization antibodies against other EV71 viral strains (Table 6).

9. Identification of linear immunodominant epitope(s) of EV71 using antisera raised against EV71 vaccine candidates Total 153 overlapping synthetic peptides were used to screen for peptides having high affinity for antisera. Among these peptides, 57 covered the VP1 protein (VP1-1 to VP1-57); 49 covered the VP2 protein (VP2-1 to VP2-49); and 47 covered the VP3 protein (VP3-1 to VP3-47).

In one experiment, six mice and three rabbits were immunized with an EV71 vaccine candidate viral stock formulated in alum. After two dosages, mice antisera were collected and pooled together. The mouse antisera showed high OD values for VP1-42 and VP1-43 peptides. The VP2 and VP3 peptides were not detected at a high OD value by the mouse antisera. Rabbit antisera showed high OD values for VP1-01, VP2-27, VP2-28, and VP2-29 peptides. The VP3 peptides were not detected at a high OD value by the rabbit antisera. The peptides having high affinities for antisera were listed in Table 7.

TABLE 7

Amino acid sequences of synthetic peptides having high affinities for antisera

| Peptide | Amino acid position | Peptide sequences |
|---|---|---|
| VP1-01 | 1-15 | GDRVADVIESSIGDS (SEQ ID NO: 5) |
| VP1-42 | 206-220 | DGYPTFGEHKQEKDL (SEQ ID NO: 6) |
| VP1-43 | 211-225 | FGEHKQEKDLEYGAC (SEQ ID NO: 7) |
| VP2-27 | 131-145 | VIGTVAGGTGTEDSH (SEQ ID NO: 8) |
| VP2-28 | 136-150 | AGGTGTEDSHPPYKQ (SEQ ID NO: 9) |
| VP2-29 | 141-155 | TEDSHPPYKQTQPGA (SEQ ID NO: 10) |

10. The alignment of EV71 VP2 epitope sequences in different subgenotypes

An EV71 VP1 sequence was aligned to a subgenotype tree. In order to understand VP2 epitope sequences from different subgenotypes (VP1-based), the VP2 amino acid sequences (131-155) of ten EV71 strains were selected and aligned. The VP2 epitope sequence alignment showed that this sequence was highly conserved among the EV71 strains (Table 8).

TABLE 8

Alignment of VP2 amino acid (131-155) sequences from different subgenotypes

| Strains | Sequences | Sub-genotype (VP1-base) |
|---|---|---|
| BrCr | VIGTVAGGTGTENSHPPYKQTQPGA (SEQ ID NO: 1) | A |
| 238/TW86 | VIGTVAGGTGTEDSHPPYKQTQPGA (SEQ ID NO: 2) | B1 |
| 7423/MS/87 | VIGTVAGGTGTEDSHPPYKQTQPGA (SEQ ID NO: 2) | B2 |
| EV71/SAR/SHA66 | VIGTVAGGTGTEDSHPPYKQTQPGA (SEQ ID NO: 2) | B3 |
| EV71/9/97/SHA89 | VIGTVAGGTGTEDSHPPYKQTQPGA (SEQ ID NO: 2) | B4 |
| 5511/SIN/00 | VIGTVAGGTGTEDSHPPYKQTQPGA (SEQ ID NO: 2) | B5 |
| 1M/AUS/12/00 | VIGTVAGGTGTEDSHPPYKQTQPGA (SEQ ID NO: 2) | C1 |
| TW/2086/98 | VIGTVAGGTGTEDSHPPYKQTQPGA (SEQ ID NO: 2) | C2 |
| SHZH98 | VIGTVAGGTGTENSHHPYKQTQPGA (SEQ ID NO: 3) | C4 |
| EV71-E59 | VIGTVAGGTGTEDSHPPYKQTQPGA (SEQ ID NO: 2) | B4 |
|  | VIGTVAGGTGTEDSHHPYKQTQPGA (SEQ ID NO: 4)* |  |

*SEQ ID NO: 4 is a sequence predicted based on SEQ ID NOs: 1-3, which two variant residues D and H.

The above-mentioned VP1-43 peptide sequence was subjected to site mutation analysis. More specifically, each of its residues (except A224) was replaced with an alanine residue to generate 14 mutant peptides. The sequences of these mutants are listed below with the alanine residue underlined. ELISA assays were then conducted to examine the ability of these 14 mutant peptides to bind to E1, a mouse anti-EV71 antibody that specifically binds to VP1-43. It was found that 215Lysine, 217Glutamic acid, 218Lysine, and 219Aspartic acid are the essential amino acids of the EV71 VP1 antigenicity.

Similarly, the above-mentioned VP2-28 peptide sequence was subjected to site mutation analysis. A set of 14 synthetic mutant peptides were generated based on the VP2-28 peptide sequence, where each amino acid residue (except 136A) was replaced by an alanine residue. The sequences of these mutants are listed below with the alanine underlined. ELISA was conducted to examine the ability of the mutants to bind to MAB979, a monoclonal antibody that specifically binds to the VP2-28 peptide. It was found that 142 Glutamic acid, 145Histidine, 148Tyrosine, and 149Lysine were essential.

| | |
|---|---|
| AGEHKQEKDLEYGAC, | SEQ ID NO: 11 |
| FAEHKQEKDLEYGAC, | SEQ ID NO: 12 |
| FGAHKQEKDLEYGAC, | SEQ ID NO: 13 |
| FGEAKQEKDLEYGAC, | SEQ ID NO: 14 |
| FGEHAQEKDLEYGAC, | SEQ ID NO: 15 |
| FGEHKAEKDLEYGAC, | SEQ ID NO: 16 |
| FGEHKQAKDLEYGAC, | SEQ ID NO: 17 |
| FGEHKQEADLEYGAC, | SEQ ID NO: 18 |
| FGEHKQEKALEYGAC, | SEQ ID NO: 19 |
| FGEHKQEKDAEYGAC, | SEQ ID NO: 20 |
| FGEHKQEKDLAYGAC, | SEQ ID NO: 21 |
| FGEHKQEKDLEAGAC, | SEQ ID NO: 22 |
| FGEHKQEKDLEYAAC, | SEQ ID NO: 23 |
| FGEHKQEKDLEYGAA, | SEQ ID NO: 24 |
| AAGTGTEDSHPPYKQ, | SEQ ID NO: 25 |
| AGATGTEDSHPPYKQ, | SEQ ID NO: 26 |
| AGGAGTEDSHPPYKQ, | SEQ ID NO: 27 |
| AGGTATEDSHPPYKQ, | SEQ ID NO: 28 |
| AGGTGAEDSHPPYKQ, | SEQ ID NO: 29 |
| AGGTGTADSHPPYKQ, | SEQ ID NO: 30 |
| AGGTGTEASHPPYKQ, | SEQ ID NO: 31 |
| AGGTGTEDAHPPYKQ, | SEQ ID NO: 32 |
| AGGTGTEDSAPPYKQ, | SEQ ID NO: 33 |
| AGGTGTEDSHAPYKQ, | SEQ ID NO: 34 |
| AGGTGTEDSHPAYKQ, | SEQ ID NO: 35 |
| AGGTGTEDSHPPAKQ, | SEQ ID NO: 36 |
| AGGTGTEDSHPPYAQ, | SEQ ID NO: 37 |
| AGGTGTEDSHPPYKA, | SEQ ID NO: 38 |

In another experiment, 10 male and 10 female CD® (SD) IGS strain rats (Groups 1 and 2, respectively) were immunized and boosted 3 weeks later i.m. with 0.5 mL of the alum-absorbed inactivated EV71-E59 viral stock. The results were summarized in Table 9 below. As shown in the table, the immunization induced antisera that had high neutralizing titers.

TABLE 9

Immunogenicity of inactivated EV71-E59 virus in a rat model.

| | Purification method | Sample | Total protein (µg/dose) | Neutralization antibody (TCID50) |
|---|---|---|---|---|
| Group-1 | Liquid Chromatography | Mix particles | 10 | 458 |
| Group-2 | Liquid Chromatography | Mix particles | 10 | 654 |

The affinity of the antisera to each of the synthetic peptides described above was measured by enzyme-linked immunosorbent assay (ELISA) in the same manner. It was found that VP1-25, VP1-42, VP1-49, VP1-50, VP2-20 and VP3-22 were detected with high OD values, suggesting that the antiseara bound to these peptides with high affinities. Listed in Table 10 below are the sequences of these peptides.

TABLE 10

Amino acid sequences of synthetic peptides having high affinities for antisera

| Peptide | Amino acid position | Peptide sequences |
|---|---|---|
| VP1-25 | 121-135 | RKVELFTYMRFDAEF (SEQ ID NO: 39) |
| VP1-49 | 241-255 | SKSKYPLVIRIYMRM (SEQ ID NO: 40) |
| VP1-50 | 246-260 | PLVIRIYMRMKHVRA (SEQ ID NO: 41) |
| VP2-20 | 96-110 | AQFHYLYRSGFCIHV (SEQ ID NO: 42) |
| VP3-22 | 106-120 | GYYTQWSGSLEVTFM (SEQ ID NO: 43) |

Sequence alignment was conducted to examine the VP1-25 amino acid sequences from different subgenotypes. The results were shown in Table 11 below. It was found that these peptides had a highly consensus sequence: RKVELFTDMRFDAEF (SEQ ID NO:44).

TABLE 11

Alignment of P1-25 amino acid sequences from different subgenotypes

| Strains | Sequences | Subgenotype (VP1-base) |
|---|---|---|
| BrCr | RKVELFTYMRFDAEF (SEQ ID NO: 39) | A |
| 238/TW86 | RKVELFTYMRFDAEF (SEQ ID NO: 39) | B1 |
| 7423/MS/87 | RKVELFTYMRFDAEF (SEQ ID NO: 39) | B2 |
| EV71/SAR/SHA66 | RKVELFTYMRFDAEF (SEQ ID NO: 39) | B3 |
| EV71/9/97/SHA89 | RKVELFTYMRFDAEF (SEQ ID NO: 39) | B4 |
| 5511/SIN/00 | RKVELFTYMRFDAEF (SEQ ID NO: 39) | B5 |
| 1M/AUS/12/00 | RKVELFTYMRFDAEF (SEQ ID NO: 39) | C1 |
| TW/2086/98 | RKVELFTYMRFDAEF (SEQ ID NO: 39) | C2 |
| SHZH98 | RKVELFTDMRFDAEF (SEQ ID NO: 44) | C4 |
| EV71 E59 | RKVELFTYMRFDAEF (SEQ ID NO: 39) | B4 |

\*\*\*\*\*\*\* \*\*\*\*\*\*\*

Similar alignment analysis was conducted on VP1-49 and VP1-50 amino acid sequences from different subgenotypes. The results were shown in Table 12 below.

TABLE 12

Alignment of VP1-49 or 50 amino acid sequences from different subgenotypes

| Strains | Sequences | Subgenotype (VP1-base) |
|---|---|---|
| BrCr | SKSEYSLVIRIYMRMKHVRA (SEQ ID NO: 47) | A |
| 238/TW86 | SKSKYPLVIRIYMRMKHVRA (SEQ ID NO: 48) | B1 |
| 7423/MS/87 | SKSKYPLVVRIYMRMKHVRA (SEQ ID NO: 49) | B2 |
| EV71/SAR/SHA66 | SKSKYPLVVRIYMRMKHVRA (SEQ ID NO: 49) | B3 |
| EV71/9/97/SHA89 | SKSKYPLVIRIYMRMKHVRA (SEQ ID NO: 49) | B4 |
| 5511/SIN/00 | SKSKYPLVVRIYMRMKHVRA (SEQ ID NO: 49) | B5 |
| 1M/AUS/12/00 | SKSKYPLVIRIYMRMKHVRA (SEQ ID NO: 48) | C1 |
| TW/2086/98 | SKSKYPLVIRIYMRMKHVRA (SEQ ID NO: 48) | C2 |
| SHZH98 | SKSKYPLVVRIYMRMKHVRA (SEQ ID NO: 49) | C4 |
| EV71 E59 | SKSKYPLVVRIYMRMKHVRA (SEQ ID NO: 49) | B4 |

\*\*\* \* \*\* \*\*\*\*\*\*\*\*\*\*\*\*

Two consensus sequences were identified: SKSKYPLVVRIYMRM (SEQ ID NO: 45) and SKSEYSLVIRIYMRM (SEQ ID NO: 46)

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. An immunogenic composition comprising an isolated and inactivated EV71-E59 virus full-particle and an isolated and inactivated EV71-E59 virus sub-particle, the inactivated full particle and the inactivated sub-particle being produced by incubating an EV71-E59 virus full-particle and an EV71-E59 virus sub-particle in a 37% formaldehyde solution, wherein the inactivated full-particle and the inactivated sub-particle each contain viral antigens that are cross-linked by the formaldehyde solution, and wherein, prior to being inactivated, (a) the full particle contains an EV71-E59 VP1 protein having a molecular weight of 36 kDa, an EV71-E59 VP2 protein having a molecular weight of 28 kDa, an EV71-E59 VP3 protein having a molecular weight of 27 kDa, and an EV71-E59 VP4 protein having a molecular weight of 8 kDa; (b) the sub-particle contains an EV71-E59 VP0 protein having a molecular weight of 38 kDa, the EV71-E59 VP1 protein having a molecular weight of 36 kDa, and the EV71-E59 VP3 protein having a molecular weight of 27 kDa; and (c) in a 10-50% continuous sucrose gradient, the full particle is detected in fractions having 35 to 38% sucrose and the sub-particle is detected in fractions having 25 to 28% sucrose, the molecular weights of the proteins being observed molecular weights on a 10% SDS-polyacrylamide gel.

2. The immunogenic composition of claim 1, wherein the immunogenic composition further comprises a pharmaceutically acceptable adjuvant.

3. The immunogenic composition of claim 2, wherein the adjuvant contains aluminum phosphate.

4. The immunogenic composition of claim 1, wherein the full particle and sub-particle arc inactivated by incubating both particles in the 37% formaldehyde solution at 20-45° C. for 2 to 20 days.

5. The immunogenic composition of claim 4, wherein both particles are incubated in the 37% formaldehyde solution at 37° C. for 2 to 5 days.

6. The immunogenic composition of claim 1, wherein the viral antigens that are cross-linked are selected from the group consisting of the EV71-E59 VP1, VP2, VP3, and VP4 proteins.

* * * * *